(12) United States Patent
Minato

(10) Patent No.: US 8,094,302 B2
(45) Date of Patent: Jan. 10, 2012

(54) SPECTROPHOTOMETER

(75) Inventor: Hiroyuki Minato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 389 days.

(21) Appl. No.: 12/488,510

(22) Filed: Jun. 19, 2009

(65) Prior Publication Data

US 2009/0316148 A1    Dec. 24, 2009

(30) Foreign Application Priority Data

Jun. 20, 2008  (JP) .................................. 2008-161545

(51) Int. Cl.
*G01N 21/64* (2006.01)
(52) U.S. Cl. ...... 356/317; 356/318; 356/417; 250/458.1
(58) Field of Classification Search .................. 356/317, 356/318, 417
See application file for complete search history.

(56) References Cited

U.S. PATENT DOCUMENTS 6,316,774 B1 * 11/2001 Giebeler et al. ........... 250/458.1

FOREIGN PATENT DOCUMENTS

JP         2000-9644 A      1/2000

* cited by examiner

*Primary Examiner* — F. L. Evans
(74) *Attorney, Agent, or Firm* — Cheng Law Group, PLLC

(57) ABSTRACT

Disclosed herein is a spectrophotometer. The spectrophotometer includes a CPU having a signal prediction part and a comparison/calculation part. The signal prediction part predicts the strength of an output signal from a photodetection unit during the next period based on the strength of the output signal from the photodetection unit. The comparison/calculation part compares a reference value, which defines the limit value of electrical current passing through a photomultiplier tube, of the strength of an output signal from an AD converter with a predicted value predicted by the signal prediction part. In a case where the predicted value exceeds the reference value, a voltage applied to the photomultiplier tube is calculated so that the strength of an output signal from the photodetection unit during the next period does not exceed the reference value. An applied voltage control part is configured to perform applied voltage control based on an applied voltage value calculated by the comparison/calculation part when the predicted value of the strength of an output signal from the photodetection unit during the next period exceeds the reference value.

9 Claims, 3 Drawing Sheets

SPECTROPHOTOMETER

BACKGROUND OF THE INVENTION

1. Field of the Invention

The present invention relates to a spectrophotometer for use as a detector for detecting sample components separated by, for example, a liquid chromatograph.

2. Description of the Related Art

A fluorospectrophotometer generally includes a sample cell, a photodetection unit, a light source, an excitation optical system, and a fluorescence optical system. An example of the sample cell includes a flow cell to be arranged downstream from an analytical column of a liquid chromatograph to allow an eluate containing sample components separated by the analytical column to flow through it. The excitation optical system is provided to extract an excitation light component from light emitted from the light source and deliver the excitation light component to the sample cell. A sample flowing through the sample cell is excited by the excitation light component and emits fluorescence. The fluorescence optical system is provided to extract a fluorescence component from light emitted from the sample cell and deliver the fluorescence component to the photodetection unit.

The photodetection unit generally has a photomultiplier tube. The photomultiplier tube produces electrons according to the amount of light incident on its entrance window due to photoelectric effect, multiplies the number of electrons, and outputs electrical current. When light enters the photomultiplier tube to which a constant voltage is being applied to keep its multiplication factor constant, electrical current of which the magnitude is proportional to the amount of light incident on the entrance window is outputted. Therefore, the amount of light incident on the entrance window can be measured by detecting the value of the output current. When the multiplication factor of the photomultiplier tube is higher, the number of electrons proportional to the amount of light incident on the photomultiplier tube is more greatly multiplied and a larger current value is outputted so that higher detection sensitivity is achieved.

However, such a photomultiplier tube has a problem that it is deteriorated when electrical current exceeding a maximum allowable limit passes through it. For example, in a case where the wavelength of excitation light and the wavelength of fluorescence are the same or close to each other, the excitation light reflected by a sample is not attenuated at all in the fluorescence optical system, or even when it is attenuated in the fluorescence optical system, the degree of attenuation is not so great. In this case, the excitation light component as well as the fluorescence emitted from the sample enters the photomultiplier tube and, therefore, the amount of light incident on the photomultiplier tube is increased, which may result in the passage of excessive electrical current through the photomultiplier tube leading to the deterioration of the photomultiplier tube.

In order to solve the above problem, a method for decreasing electrical current passing through a photomultiplier tube has been proposed (see, for example, Japanese Patent Application Laid-open No. 2000-9644). More specifically, the limit-current-value of a photomultiplier tube is defined as a threshold value, and electrical current outputted from the photomultiplier tube is compared with the threshold value. When the output electrical current exceeds the threshold value, a voltage applied to the photomultiplier tube is decreased to reduce the multiplication factor of the photomultiplier tube so that electrical current passing through the photomultiplier tube is decreased. It is to be noted that the limit-current-value of the photomultiplier tube refers to a maximum level of electrical current that can pass through the photomultiplier tube without deteriorating the photomultiplier tube.

However, in the case of using such a method, since a voltage applied to the photomultiplier tube is decreased after electrical current outputted from the photomultiplier tube exceeds the limit-current-value, electrical current exceeding the limit-current-value passes through the photomultiplier tube for any length of time, and therefore, the deterioration of the photomultiplier tube is to some degree inevitable. Even in the case of using this method, the multiplication factor of the photomultiplier tube can be reduced before electrical current passing through the photomultiplier tube exceeds the limit-current-value by selecting a threshold value lower than the limit-current-value. However, in this case, it is impossible to maximize the sensitivity of the photomultiplier tube.

SUMMARY OF THE INVENTION

It is therefore an object of the present invention to prevent the passage of excessive electrical current through a photomultiplier tube of a spectrophotometer leading to the deterioration of the photomultiplier tube without reducing the sensitivity of the photomultiplier tube.

In order to achieve the above object, the present invention is directed to a spectrophotometer including, a light source; a sample cell; an excitation optical system for extracting an excitation light component from light emitted from the light source and delivering the excitation light component to the sample cell; a fluorescence optical system for extracting a fluorescence component from light emitted from the sample cell; a photodetection unit for detecting a fluorescence component extracted by the fluorescence optical system; a signal prediction part; and a control unit.

The photodetection unit has a photomultiplier tube and outputs a signal corresponding to the amount of light detected by the photomultiplier tube at a constant frequency.

The signal prediction part predicts the strength of an output signal from the photodetection unit during subsequent periods per period sequentially based on the output signal from the photodetection unit.

The control unit adjusts a voltage applied to the photomultiplier tube based on a predicted value predicted by the signal prediction part so that the strength of an output signal from the photodetection unit during subsequent periods does not exceed a reference value of the strength of an output signal from the photodetection unit. The reference value defines the limit of electrical current passing through the photomultiplier tube.

In a case where the predicted value exceeds the reference value, the control unit adjusts a voltage applied to the photomultiplier tube based on the predicted value by, for example, the following method. According to a first embodiment, the control unit decreases a voltage applied to the photomultiplier tube by a first voltage so that the predicted value becomes equal to the reference value. According to a second embodiment, the control unit decreases a voltage applied to the photomultiplier tube by a first voltage so that the predicted value becomes equal to the reference value, and further decreases the determined voltage applied to the photomultiplier tube by a predetermined second voltage. In this case, the second voltage is preferably selected from among two or more different voltages set by the control unit.

As described above, according to the present invention, since the signal prediction part predicts the strength of an output signal from the photodetection unit during subsequent periods per period sequentially based on the output signal from the photodetection unit and the control unit adjusts a voltage applied to the photomultiplier tube based on a predicted value predicted by the signal prediction part so that the strength of an output signal from the photodetection part during subsequent periods does not exceed the reference value, electrical current passing through the photomultiplier tube can be decreased by reducing the multiplication factor of the photomultiplier tube before excessive electrical current passes through the photomultiplier tube. This makes it possible to prevent the deterioration of the photomultiplier tube.

A peak curve in a chromatogram obtained by detecting sample components separated by a liquid chromatograph declines after reaching its peaks, and therefore, in a case where the multiplication factor of the photomultiplier tube is temporarily reduced around a peak and is then kept at a reduced level, the sensitivity of the photomultiplier tube remains lower than its maximum, which leads to reduced accuracy of subsequent measurements. Therefore, in a case where the multiplication factor of the photomultiplier tube is temporarily reduced, it is preferred that, when it is predicted that the photomultiplier tube is not deteriorated even when the multiplication factor of the photomultiplier tube is returned to its original level, the multiplication factor of the photomultiplier tube is returned to its original level. This makes it possible to maximize the sensitivity of the photomultiplier tube.

More specifically, according to a preferred embodiment of the present invention, in a case where a predicted value predicted by the signal prediction part is an output signal strength predicted after a voltage applied to the photomultiplier tube is adjusted to be lower than a predetermined voltage (which is defined as a first predicted value), the signal prediction part predicts an output signal strength during the same period as the first predicted value on the assumption that the voltage applied to the photomultiplier tube is returned to the predetermined voltage (which is defined as a second predicted value). In this case, when the second predicted value does not exceed the reference value, the control unit preferably returns the voltage applied to the photomultiplier tube to the predetermined voltage at a timing corresponding to this period.

The signal prediction part may predict the strength of an output signal from the photodetection unit during subsequent periods per period sequentially based on the difference in output signal strength between the current period and the last period or based on an approximate expression created using output signal strengths during two or more periods.

DETAILED DESCRIPTION OF THE INVENTION

Figure 1:
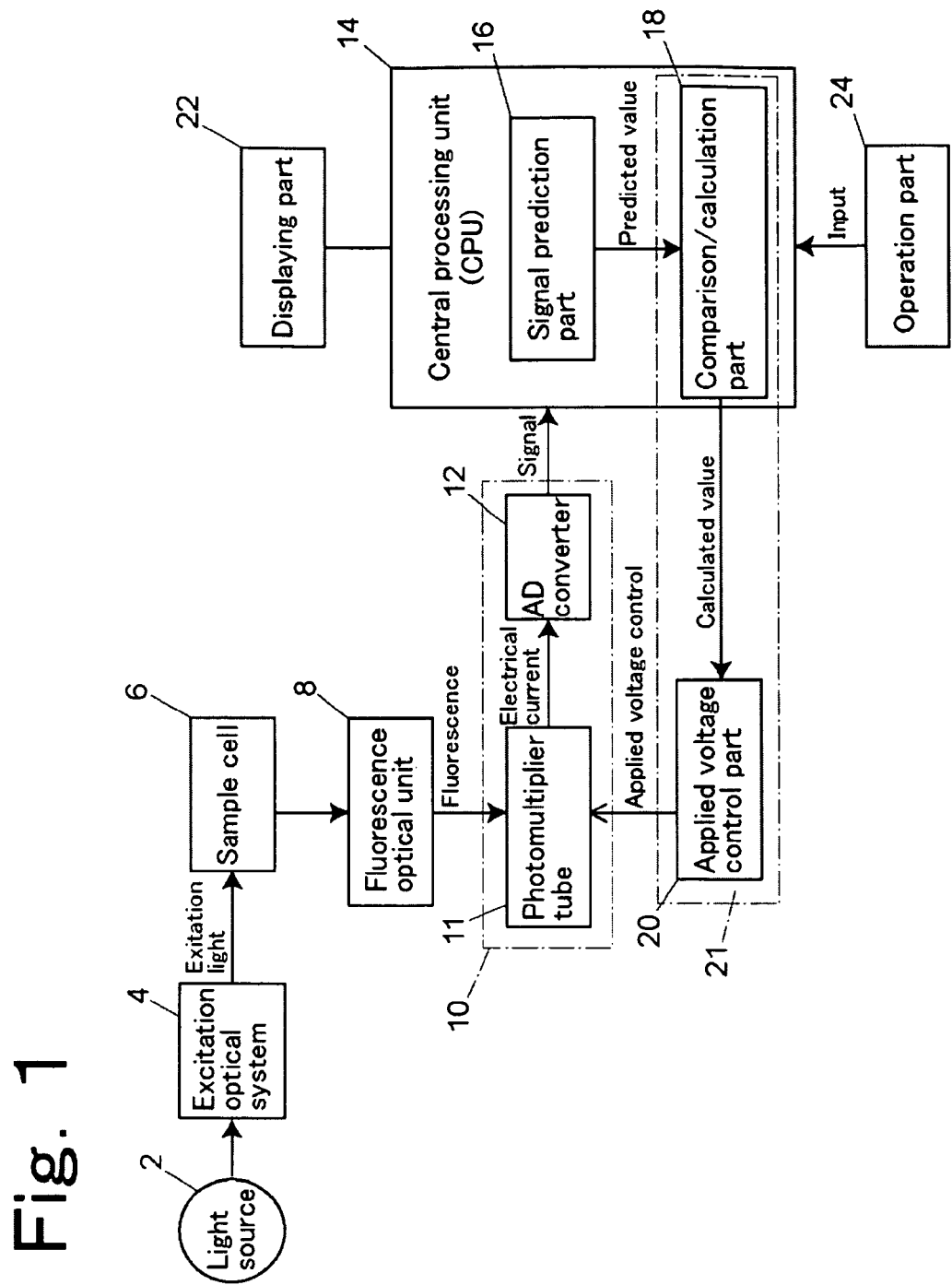
FIG. 1 is a schematic block diagram of one embodiment of a spectrophotometer according to the present invention.

Hereinbelow, one embodiment of a spectrophotometer according to the present invention will be described with reference to FIG. 1.

A sample such as an eluate eluted from an analytical column of a liquid chromatograph flows through a sample cell (flow cell) 6. The sample flowing through the sample cell 6 is irradiated with an excitation light component extracted by an excitation optical system 4 from tight emitted from a light source 2. The sample is excited by excitation light and emits fluorescence, and the fluorescence is delivered by a fluorescence optical system 8 to a photomultiplier tube 11 of a photodetection unit 10 and then detected by the photomultiplier tube 11.

More specifically, the excitation optical system 4 separates light emitted from the light source 2 with the use of, for example, a diffraction grating to extract an excitation light component, and delivers the excitation light component to the sample cell 6. It is preferred that the excitation optical system 4 can switch among different wavelengths of light to be delivered to the sample cell 6 as excitation light to select a desired wavelength according to a sample that flows through the sample cell 6.

The fluorescence optical system 8 separates light emitted from the sample cell 6 with the use of for example, a diffraction grating to extract light having a fluorescence wavelength to be detected, and delivers the light to the photomultiplier tube 11. It is preferred that the fluorescence optical system 8 can switch among different wavelengths of light to be delivered to the photomultiplier tube 11 as fluorescence to select a desired wavelength according to a sample that flows through the sample cell 6.

The photomultiplier tube 11 has a photoelectric surface that produces photoelectrons by irradiation with light. The photoelectric surface is arranged so as to be able to receive light from the fluorescence optical system 8. The photomultiplier tube 11 multiplies photoelectrons proportional to the amount of incident light from the fluorescence optical system 8 and outputs electrical current. The photodetection unit 10 has an AD converter 12 that outputs a signal with strength corresponding to the magnitude of electrical current outputted from the photomultiplier tube 11 at a constant frequency. The AD converter 12 is connected to a central processing unit (CPU) 14.

The CPU 14 has a signal prediction part 16 and a comparison/calculation part 18. The signal prediction part 16 predicts the strength of an output signal from the photodetection unit 10 during subsequent periods per period sequentially based on the strength of the output signal from the photodetection unit 10. The comparison/calculation part 18 stores a reference value of the strength of an output signal from the AD converter 12. The reference value defines the limit value of electrical current passing through the photomultiplier tube 11. The comparison/calculation part 18 compares a predicted value predicted by the signal prediction part 16 with the reference value. As a result of the comparison, in a case where the predicted value exceeds the reference value, the comparison/calculation part 18 calculates a voltage applied to the photomultiplier tube 11 so that an output signal strength during the next period does not exceed the reference value. An applied voltage control part 20 adjusts a voltage applied to the photomultiplier tube 11. More specifically, the applied voltage control part 20 applies a predetermined voltage to the photomultiplier tube 11 but, when it is predicted that the strength of an output signal from the photodetection unit 10 during the next period exceeds the reference value, it performs applied voltage control so that a voltage applied to the photomultiplier tube 11 is adjusted to an applied voltage value calculated and outputted by the comparison/calculation part 18. The comparison/calculation part 18 and the applied voltage control part 20 constitute a control unit 21 of the spectrophotometer according to the present invention.

The CPU 14 has, in addition to the above functions the function of displaying measured data on a displaying part 22 based on the strength of an output signal from the photodetection unit 10 and the function of controlling the operations of the light source 2, the excitation optical system 4 and the fluorescence optical system 8 based on instructions inputted by an analyst through an operation part 24.

Figure 2:
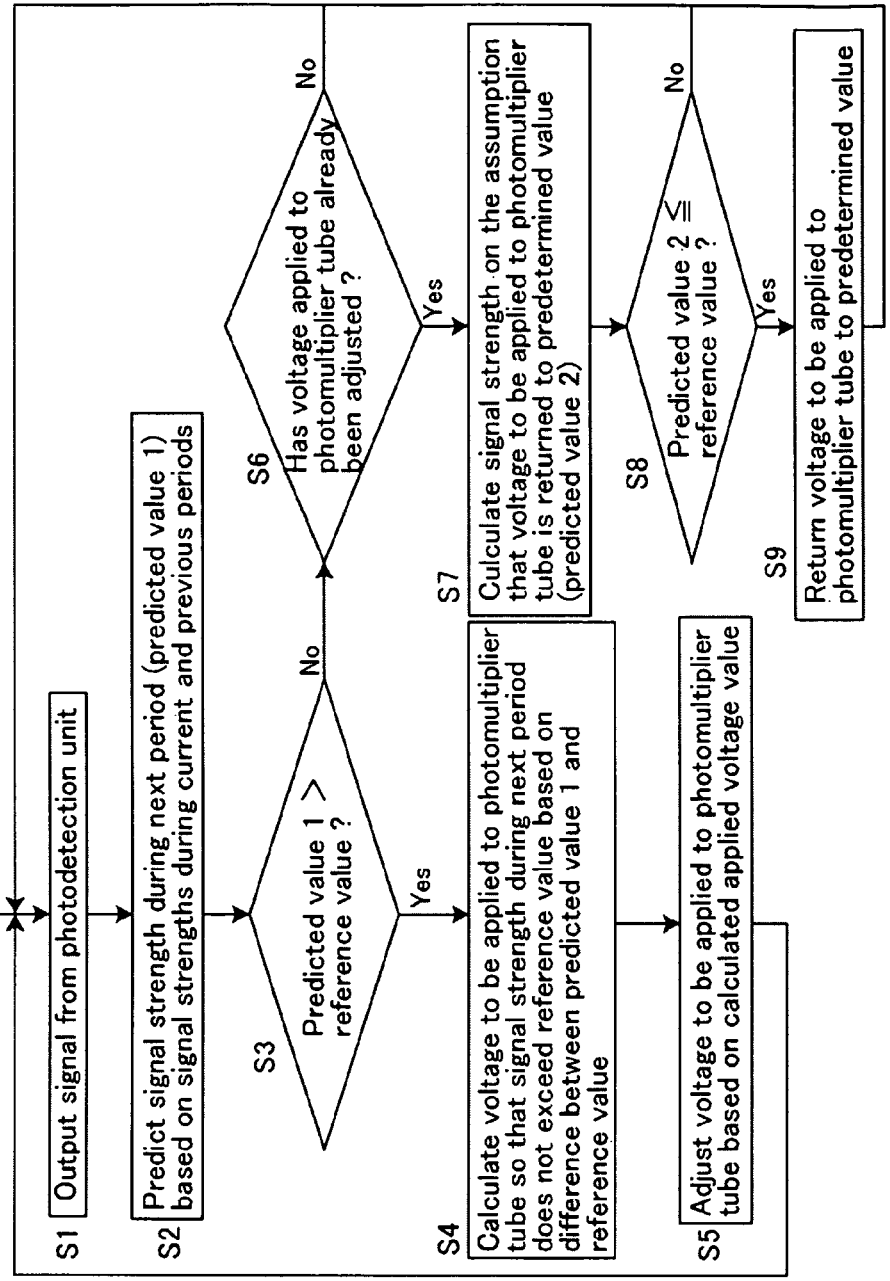
FIG. 2 is a flow chart showing the operation of controlling a voltage applied to a photomultiplier tube.
Figure 3:
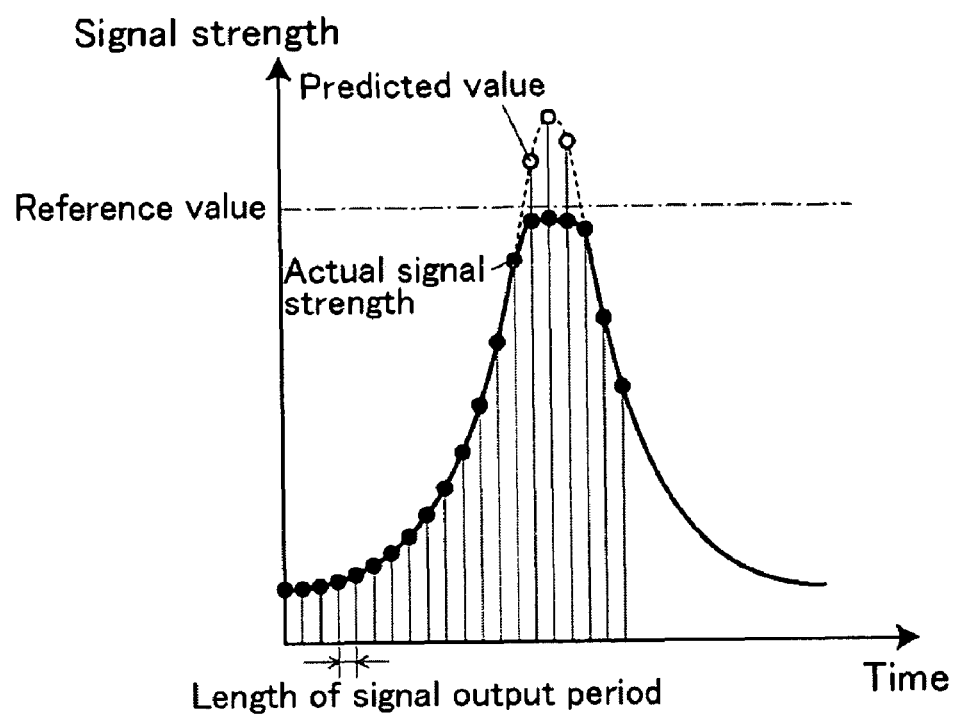
FIG. 3 is a graph showing one example of a change in the strength of an output signal from a photodetection unit with time.

Hereinbelow, an example of the operation of controlling a voltage applied to the photomultiplier tube 11 of the spectrophotometer according to this embodiment will be described with reference to FIGS. 2 and 3. FIG. 2 is a flow chart showing the operation of controlling a voltage applied to the photomultiplier tube, and FIG. 3 is a graph showing an example of a change in the strength of an output signal from the photodetection unit with time.

It is to be noted that the operation of controlling a voltage applied to the photomultiplier tube 11 will be described below with reference to a case where the strength of a signal from the photodetection unit 10 during the next period is predicted as a predicted value based on signal strengths during current and previous periods, and a voltage applied to the photomultiplier tube 11 is adjusted based on the predicted value before the next period's signal output is produced. However, the present invention is not limited to this case, and the operation of controlling a voltage applied to the photomultiplier tube 11 may be performed in the following manner. More specifically, a signal strength during one period after the next period is predicted as a predicted value based on signal strengths during two or more previous periods, and a voltage applied to the photomultiplier tube 11 so that a signal strength during a period after the next does not exceed the reference value is previously calculated based on the predicted value. Then, when the time comes to adjust a voltage applied to the photomultiplier tube 11, a voltage applied to the photomultiplier tube 11 is adjusted to the previously calculated one.

First, fluorescence emitted from a sample contained in the sample cell 6 irradiated with excitation light is extracted by the fluorescence optical system 8, and is then allowed to enter the photomultiplier tube 11 of the photodetection unit 10. At this time, a predetermined negative high voltage (hereinafter, referred to as a "predetermined value") has been applied to the photomultiplier tube 11 to allow the photomultiplier tube 11 to have a certain multiplication factor. When the photomultiplier tube 11 is irradiated with light photoelectrons proportional to the amount of incident light are produced and multiplied by the certain multiplication factor so that electrical current is outputted to the AD converter 12. The AD converter 12 outputs a signal with strength corresponding to the electrical current from the photomultiplier tube 11 to the CPU 14 at a constant frequency (Step 1).

The signal prediction part 16 of the CPU 14 predicts the strength of a signal from the AD converter 12 during the next period based on signal strengths during current and previous periods (Step 2). Examples of a method for predicting a signal strength include a method in which the strength of a signal during the next period is predicted based on the difference in signal strength (i.e. signal strength gradient) between the current period and the last period and a method in which the strength of a signal during subsequent periods is predicted per period sequentially based on an approximate expression created using signal strengths during two or more periods. It is to be noted that a predicted value predicted by the signal prediction part 16 in the Step 2 is defined as "predicted value 1".

The comparison/calculation part 18 compares the predicted value 1 predicted by the signal prediction part 16 with the reference value previously stored therein (Step 3).

As a result of the comparison, in a case where the predicted value 1 exceeds the reference value, a voltage applied to the photomultiplier tube 11 so that the strength of a signal from the AD converter 12 during the next period does not exceed the reference value is calculated by the comparison/calculation part 18 based on the difference between the predicted value 1 and the reference value and is outputted as a calculated value (Step 4). The applied voltage control unit 20 adjusts a voltage applied to the photomultiplier tube 11 based on the calculated value calculated by the comparison/calculation part 18 to reduce the multiplication factor of the photomultiplier tube 11 (Step 5). The signal prediction part 16 waits for the next period's signal output from the photodetection unit 10.

The strength of an output signal from the AD converter 12 corresponds to the magnitude of output electrical current from the photomultiplier tube 11. The output electrical current from the photomultiplier tube 11 is determined by the amount of light incident on the photomultiplier tube 11 and the multiplication factor of the photomultiplier tube 11. Therefore, the output electrical current from the photomultiplier tube 11 can be decreased by reducing the multiplication factor of the photomultiplier tube 11. The relationship between an applied voltage (negative high voltage) and a multiplication factor specific to the photomultiplier tube 11 is previously determined and stored in the comparison/calculation part 18. The comparison/calculation part 18 determines a voltage applied to the photomultiplier tube 11 based on the relationship between an applied voltage and a multiplication factor of the photomultiplier tube 11 and the predicted value so that the strength of a signal from the AD converter 12 during the next period is close to, but not more than, the reference value.

On the other hand, in a case where the predicted value 1 is equal to or less than the reference value, it is determined whether or not a voltage applied to the photomultiplier tube 11 is the predetermined value, that is, whether or not a voltage applied to the photomultiplier tube 11 has been adjusted in the Step 4 and Step 5 (Step 6). When a voltage applied to the photomultiplier tube 11 is the predetermined value, it is not necessary to perform any adjustments on the voltage applied to the photomultiplier tube 11. Then, the signal prediction part 16 waits for the next period's signal output from the photodetection unit 10.

On the other hand, when a voltage applied to the photomultiplier tube 11 is not the predetermined value, that is, when a voltage applied to the photomultiplier tube 11 has already been adjusted in the Step 4 and Step 5, the signal prediction part 16 predicts, as a predicted value 2, a signal strength on the assumption that the voltage applied to the photomultiplier tube 11 is returned to the predetermined value (Step 7). Then, the comparison/calculation part 18 compares the predicted value 2 with the reference value (Step 8). When the predicted value 2 is equal to or less than the reference value, the applied voltage control part 20 returns the voltage applied to the photomultiplier tube 11 to the predetermined value, and then the signal prediction part 16 waits for the next period's signal output from the photodetection unit 10. On the other hand, when the predicted value 2 exceeds the reference value, the adjusted voltage is still applied to the photomultiplier tube 11, and then the signal prediction part 16 waits for the next period's signal output from the photodetection unit 10.

The determination of a voltage applied to the photomultiplier tube 11 based on the predicted value 1 is performed by, for example, the following method. The predetermined voltage (negative high voltage) applied to the photomultiplier tube 11 is defined as −PV. An AD converter providing a 16-bit output is used as the AD converter 12. In this case, a range between 0V to −PV is divided into 65536 points so that the negative high voltage can vary by one point which corresponds to a voltage (V) represented by (P/65536). The comparison/calculation part 18 calculates the amount of decrease in the negative high voltage (i.e., the number of points α) so that the predicted value given by the signal prediction part 16 becomes equal to the reference value. It is to be noted that since a voltage applied to the photomultiplier tube 11 is a negative high voltage, the term "decrease" means decrease in the absolute value of the voltage toward 0 V. The value α can be calculated based on the relationship between the negative high voltage applied to the photomultiplier tube 11 and the multiplication factor of the photomultiplier tube 11 which is stored in the comparison/calculation part 18. More specifically, a factor (k) representing the rate of a change in the output value (X) of the photomultiplier tube 11 with respect to a change in the negative high voltage applied to the photomultiplier tube 11 is previously determined by measurement, and the value α is calculated by the following formula (1):

$$\alpha = kX \tag{1}$$

According to a first embodiment the predetermined voltage (−PV) applied to the photomultiplier tube 11 is decreased by the number of points α calculated based on the predicted value so that an actual negative high voltage becomes [−(P−α)]V.

According to a second embodiment, the predetermined voltage (−PV) applied to the photomultiplier tube 11 is decreased by the number of points α calculated based on the predicted value and is further decreased by the number of points β to more reliably prevent the strength of the next period's signal output from exceeding the reference value. In this case, an actual negative high voltage becomes [−(P−(α+β))]V. The number of points β can be represented by, for example, β=α/2.

Further, the number of points β can be set so as to vary according to the situation. For example, the number of points β can be set so as to be larger when the wavelength of the excitation light and the wavelength of the fluorescence are close to each other (for example within 5 nm) or a change in light intensity is large. This can be achieved by, for example, setting the following three states in the CPU 14.

$$\beta = \alpha \times (\tfrac{1}{2}) \quad \text{(State 1)}$$

$$\beta = \alpha \times 1 \quad \text{(State 2)}$$

$$\beta = \alpha \times 2 \quad \text{(State 3)}$$

In this case, a user is allowed to select the value β from the above three choices by operating the operation part 24. By allowing the magnitude of decrease in a voltage applied to the photomultiplier tube 11 to be selected based on the predicted value, it is possible to effectively prevent the value of electrical current passing through the photomultiplier tube 11 from exceeding the limit-current-value even when the wavelength of the excitation light and the wavelength of the fluorescence are close to each other or a change in light intensity is large.

As has been described above, the operation of controlling a voltage applied to the photomultiplier tube 11 is performed in the following manner. The strength of an output signal from the AD converter 12 during the next period is predicted as a predicted value based on output signal strengths during current and previous periods corresponding to the magnitude of output electrical current from the photomultiplier tube 11. When the predicted value exceeds the reference value, a voltage applied to the photomultiplier tube 11 is adjusted to reduce the multiplication factor of the photomultiplier tube 11 to decrease the output electrical current from the photomultiplier tube 11 so that the strength of the next period's signal output does not exceed the reference value. This makes it possible to reduce the multiplication factor of the photomultiplier tube 11 before excessive electrical current passes through the photomultiplier tube 11, thereby preventing the deterioration of the photomultiplier tube 11.

In a case where a voltage applied to the photomultiplier tube 11 is controlled in such a manner as described above, it is possible to obtain a peak waveform represented by, for example, the solid line shown in FIG. 3 which is a graph showing a change in the strength of an output signal from the photodetection unit 10 with time. In the case of the graph shown in FIG. 3, it was predicted that signal strengths during three periods near the peak of the waveform would exceed the reference value based on signal strengths during previous periods, but signal strengths close to but less than the reference value were actually detected as a result of the correction of the multiplication factor of the photomultiplier tube 11. As can be seen from the graph shown in FIG. 3, in this case, if the negative high voltage applied to the photomultiplier tube is kept constant, a signal strength represented by the peak waveform exceeds the reference value during a certain period of time. However, in fact, the signal strength does not exceed the reference value during any periods because the negative high voltage applied to the photomultiplier tube is decreased. Therefore excessive electrical current does not pass through the photomultiplier tube 11 and therefore the deterioration of the photomultiplier tube 11 can be prevented.

It is to be noted that in the case of such a spectrophotometer as described above, when the excitation wavelength selected by the excitation optical system 4 and the fluorescence wavelength selected by the fluorescence optical system 8 are the same or close to each other, the amount of light incident on the photomultiplier tube 11 is larger than other cases and therefore there is a stronger possibility that excessive electrical current passes through the photomultiplier tube 11. In order to prevent the passage of excessive electrical current through the photomultiplier tube 11, the predicted value 1 predicted by the signal prediction part 16 may be multiplied by a factor larger than 1 to increase the predicted value 1 only when the excitation wavelength selected by the excitation optical system 4 and the fluorescence wavelength selected by the fluorescence optical system 8 are the same or close to each other. As a result, this lowers the level of a criterion by which to judge whether a voltage applied to the photomultiplier tube 11 is adjusted thereby more reliably preventing the passage of excessive electrical current through the photomultiplier tube 11. In this case, it is also possible to maximize the sensitivity of the photomultiplier tube 11 because the level of a criterion by which to judge whether a voltage applied to the photomultiplier tube 11 is adjusted is lowered only when there is a strong possibility that excessive electrical current passes through the photomultiplier tube 11.

What is claimed is:

1. A spectrophotometer comprising:
    a light source;
    a sample cell;
    an excitation optical system for extracting an excitation light component from light emitted from the light source and delivering the excitation light component to the sample cell;
    a fluorescence optical system for extracting a fluorescence component from light emitted from the sample cell;
    a photodetection unit having a photomultiplier tube for detecting a fluorescence component extracted by the fluorescence optical system, the photodetection unit outputting a signal corresponding to an amount of light detected by the photomultiplier tube at a constant frequency;

a signal prediction part for predicting a strength of an output signal from the photodetection unit during subsequent periods per period sequentially based on the output signal from the photodetection part; and a control unit for adjusting a voltage applied to the photomultiplier tube based on a predicted value predicted by the signal prediction part so that a strength of an output signal from the photodetection unit during subsequent periods does not exceed a reference value of a strength of an output signal from the photodetection unit which defines a limit of electrical current passing through the photomultiplier tube.

2. The spectrophotometer according to claim 1, wherein when the predicted value exceeds the reference value, the control unit decreases a voltage applied to the photomultiplier tube by a first voltage so that the predicted value becomes equal to the reference value.

3. The spectrophotometer according to claim 1, wherein when the predicted value exceeds the reference value, the control unit decreases a voltage applied to the photomultiplier tube by a first voltage so that the predicted value becomes equal to the reference value and further decreases the determined voltage applied to the photomultiplier tube by a predetermined second voltage.

4. The spectrophotometer according to claim 3, wherein the second voltage is selected from among two or more different voltages set by the control unit.

5. The spectrophotometer according to claim 1,
wherein when the predicted value is a first predicted value which is an output signal strength predicted after a voltage applied to the photomultiplier tube is adjusted to be lower than a predetermined voltage, the signal prediction part predicts, as a second predicted value, an output signal strength during the same period as the first predicted value on an assumption that the voltage applied to the photomultiplier tube is returned to the predetermined voltage, and wherein when the second predicted value does not exceed the reference value, the control unit returns the voltage applied to the photomultiplier tube to the predetermined voltage at a timing corresponding to this period.

6. The spectrophotometer according to claim 2, wherein the signal prediction part predicts a strength of an output signal from the photodetection unit during subsequent periods per period sequentially based on a difference in output signal strength between a current period and a last period.

7. The spectrophotometer according to claim 2, wherein the signal prediction part predicts a strength of an output signal from the photodetection unit during subsequent periods per period sequentially based on an approximate expression created using output signal strengths during two or more periods.

8. The spectrophotometer according to claim 1, wherein the signal prediction part predicts a strength of an output signal from the photodetection unit during subsequent periods per period sequentially based on a difference in output signal strength between a current period and a last period.

9. The spectrophotometer according to claim 1, wherein the signal prediction part predicts a strength of an output signal from the photodetection unit during subsequent periods per period sequentially based on an approximate expression created using output signal strengths during two or more periods.

* * * * *